United States Patent
Guo et al.

(10) Patent No.: US 11,441,982 B2
(45) Date of Patent: Sep. 13, 2022

(54) VARIABLE DIP FAULT SLIP SIMULATION TEST METHOD

(71) Applicant: SHANDONG UNIVERSITY OF SCIENCE AND TECHNOLOGY, Qingdao (CN)

(72) Inventors: Weiyao Guo, Qingdao (CN); Yan Tan, Qingdao (CN); Tongbin Zhao, Qingdao (CN); Yunliang Tan, Qingdao (CN); Dongxiao Zhang, Qingdao (CN)

( * ) Notice: Subject to any disclaimer, the term of this patent is extended or adjusted under 35 U.S.C. 154(b) by 0 days.

(21) Appl. No.: 17/575,150

(22) Filed: Jan. 13, 2022

(65) Prior Publication Data

US 2022/0178802 A1 Jun. 9, 2022

Related U.S. Application Data

(63) Continuation of application No. PCT/CN2020/140272, filed on Dec. 28, 2020.

(30) Foreign Application Priority Data

Dec. 9, 2020 (CN) .......................... 202011447595.7

(51) Int. Cl.
*G01N 3/08* (2006.01)
*G01N 3/06* (2006.01)
*G01N 33/24* (2006.01)

(52) U.S. Cl.
CPC ................. *G01N 3/08* (2013.01); *G01N 3/06* (2013.01); *G01N 33/24* (2013.01); *G01N 2203/0003* (2013.01); *G01N 2203/0019* (2013.01); *G01N 2203/0658* (2013.01)

(58) Field of Classification Search
CPC .... G01N 3/08; G01N 3/06; G01N 2203/0003; G01N 2203/0019; G01N 2203/0658; G01N 33/24; G01L 1/28
See application file for complete search history.

(56) References Cited

U.S. PATENT DOCUMENTS 4,715,212 A 12/1987 Johanson
2021/0302292 A1* 9/2021 Boul ........................ G01N 3/24

FOREIGN PATENT DOCUMENTS

| CN | 101930686 A | 12/2010 |
|----|-------------|---------|
| CN | 103105309 A | 5/2013 |
| CN | 107064467 A | 8/2017 |
| CN | 207051126 U | 2/2018 |
| CN | 109765086 A | 5/2019 |
| CN | 109839315 A | 6/2019 |
| CN | 110006758 A | 7/2019 |

(Continued)

*Primary Examiner* — Jonathan M Dunlap (57) ABSTRACT

The disclosure provides a variable dip fault slip simulation test method, which relates to the technical field of indoor simulation test of underground engineering. The variable dip fault slip simulation test method of the disclosure adopts a sample device and a loading device, which includes the following steps: Step 1. sample preparation; Step 2. sample assembly; Step 3. loading preparation; Step 4. sample loading. The variable dip fault slip simulation test method of the disclosure can prepare rock like samples with different dip interfaces, simulate the slip failure process of faults with different dip angles, as well as the normal dip slip and reverse dip slip of faults, facilitate the operation of slip simulation test, and collect test data automatically and accurately.

7 Claims, 8 Drawing Sheets

(56) References Cited

FOREIGN PATENT DOCUMENTS

| CN | 110333136 | A |   | 10/2019 |           |
|----|-----------|---|---|---------|-----------|
| CN | 111081110 | A | * | 4/2020  |           |
| CN | 112461668 | A | * | 3/2021  |           |
| CN | 112630412 | A | * | 4/2021  | ……… G01M 99/007 |

* cited by examiner

VARIABLE DIP FAULT SLIP SIMULATION TEST METHOD

CROSS-REFERENCE TO RELATED APPLICATIONS

This application is a continuation of International Application No. PCT/CN2020/140272 with a filling date of Dec. 28, 2020, designating the United states, now pending, and further claims to the benefit of priority from Chinese Application No. 202011447595.7 with a filing date of Dec. 9, 2020. The content of the aforementioned applications, including any intervening amendments thereto, are incorporated herein by reference.

TECHNICAL FIELD

The disclosure relates to the technical field of indoor simulation test of underground engineering, in particular to a variable dip fault slip simulation test method.

BACKGROUND

Fault is one of the important geological factors affecting the production process of coal mine. The existence of fault geological structure not only affects the mine field division, development system layout and roadway excavation of coal mine production, but also poses a major threat to the safety production and economic benefits of coal mine. The coal mining near the fault causes the change of local stress field, makes the fault activate or energy accumulate, and may eventually lead to the occurrence of rockburst. Therefore, the study on the physical and mechanical behavior of fault slip process is of great significance to the mining design near the fault, the stability control of roadway surrounding rock and the mechanism of fault rockburst.

Most of the test devices used to simulate faults are based on similar simulation tests and horizontal shear tests of rock (rock-like) samples. The model of similar simulation test can not be completely similar to the original model in terms of physical and mechanical parameters and stress conditions of materials, and the boundary conditions of the model are simple. In addition, the magnitude of horizontal stress depends on the top load, so it can not realize biaxial and true triaxial experiments with given confining pressure. Although the horizontal shear test of rock samples is not easy to simulate the complex geological conditions of multi strata, it can simulate the determined stress boundary conditions, and can study the mechanical behavior of rock samples and weakness planes under different stress loading conditions.

At present, most of the tests simulating fault slip are horizontal shear tests of rock samples and biaxial or triaxial compression tests with fixed dip angle, which can not simulate fault slip with different dip angles. The impact risk of mining near the fault is related not only to the mining location, but also to the dip angle of the fault.

SUMMARY OF THE INVENTION

The objective of the disclosure is to provide a variable dip fault slip simulation test method, which can prepare rock-like samples with different dip interfaces and simulate the slip failure process of different dip faults, so as to study the sliding conditions of different dip faults and the mechanical behavior in the slip process.

The technical solution of the disclosure is as follows:

A variable dip fault slip simulation test method, which is characterized in that a sample device and a loading device are adopted;

the sample device comprises a bottom plate, a sliding partition plate, a combined pressing plate and a rotating baffle; front and rear edges of the bottom plate are provided with sliding grooves, left and right sides of the bottom plate are provided with the sliding partition plates, front and rear ends of the the sliding partition plates are provided with sliding blocks, and the sliding blocks are slidably connected in the sliding grooves; the front and rear sides of the bottom plate are provided with the combined pressing plates, wherein the combined pressing plates are formed by splicing a plurality of the pressing blocks from head to tail, and two ends of the combined pressing plate are spliced with ends of the sliding partition plate; a rotating baffle is arranged at a middle position of the bottom plate, wherein the rotating baffle comprises a fixed plate and a sliding plate, the fixed plate is rotatably connected with the middle position of the bottom plate and the fixed plate is detachably connected with the bottom plate, and both sides of the fixed plate are slidably connected with a sliding plate; an end of the sliding plate is provided with a positioning member, wherein the positioning member is detachably connected with the combined pressing plate;

the loading device comprises a loading support platform, a top loading indenter, a top pressure bearing unit, a bottom loading indenter, a side loading indenter, a side pressure bearing unit, a bearing seat, a strain gauge, an acoustic emission detector, a computer and a camera; the loading support platform comprises a base, a left loading support frame, a right loading support frame and an upper loading support frame; the left and right sides of the base are respectively provided with the left loading support frame and the right loading support frame, and the upper loading support frame is provided on the left loading support frame and the right loading support frame; a top loading indenter is arranged on the upper loading support frame; the top bearing unit comprises a force transfer column, a roller and an upper pressure bearing plate, an upper end of the force transfer column is connected with the top loading indenter, a lower end of the force transfer column is rotated side by side and is connected with a plurality of rollers, and one side of the upper pressure bearing plate is provided with a baffle bent downward; the bottom loading indenter is set on the base; the bearing seat is arranged on the left loading support frame, and a right end of the bearing seat is rotated side by side from top to bottom to connect a plurality of rollers; a side loading indenter is arranged on the right loading support frame; the side pressure bearing unit comprises a guide shaft, a linear bearing, a side pressure bearing plate and the rollers, the guide shaft is arranged on a right side of the base, the linear bearing is arranged on the guide shaft, the side pressure bearing plate is arranged on the linear bearing, and a left end of the side pressure bearing plate is rotated side by side from top to bottom to connect a plurality of rollers;

the method comprises the following steps:

Step 1. Sample Preparation rotating the fixed plate to a preset angle to simulate the fault inclination with the preset angle, so as to make the sliding plate stretch out and draw back relative to the fixed plate; connecting the sliding plate with the combined pressing plate for positioning through the positioning member; wherein the bottom plate, the sliding partition plate and the combined pressing plate form a semi-enclosed cavity, and the rotating baffle separates the semi-enclosed cavity into two cavities; applying lubricating oil on an upper surface of the bottom plate, an inner wall of the sliding partition plate, an inner wall of the combined pressing plate, and a surface of the rotating baffle, injecting a first type of rock material into the two cavities, removing the rotating baffle and the bottom plate after the first type of rock material solidifies into a rock-like sample, removing the lubricating oil on the surface of the rock-like sample, and maintaining the rock-like sample;

wherein, the first type of rock material injected into the two cavities is the same material or different materials;

Step 2. Sample Assembly defining the rock-like sample in the cavity behind the rotating baffle as a footwall sample, and defining the rock-like sample in the cavity in front of the rotating baffle as the hanging wall sample, and the footwall sample and the hanging wall sample together form the rock-like sample; an overlapping interface between the footwall sample and the hanging wall sample is a fault interface, placing the combined pressing plates on upper and lower sides of the rock-like samples, placing the sliding partition plates on left and right sides of rock-like samples, splicing the combined pressing plate with the the sliding partition plate, wherein the combined pressing plate is disconnected at the fault interface;

Step 3. Loading Preparation in the rock-like samples, placing the footwall sample at the lower left and the hanging wall sample at the upper right, wherein the combined pressing plate on the lower side of the footwall sample is attached to the bottom loading indenter, the sliding partition plate on the left side of the footwall sample is attached to a plurality of the rollers on the bearing seat; placing the top pressure bearing unit on the upper side of the hanging wall sample, wherein the combined pressing plate on the upper side of the hanging wall sample is attached to the upper pressure bearing plate, the top position of the sliding partition plate on the right side of the hanging wall sample is attached to the baffle, and the other positions except the top position of the sliding partition plate on the right side of the hanging wall sample are attached to the plurality of rollers on the side pressure bearing plate;

or, in the rock-like samples, placing the footwall sample at the lower right and the hanging wall sample at the upper left; wherein the combined pressing plate on the lower side of the hanging wall sample is attached to the bottom loading indenter, and the sliding partition plate on the left side of the hanging wall sample is attached to the plurality of the rollers on the bearing seat; placing the top pressure bearing unit on the upper side of the footwall sample, wherein the combined pressing plate on the upper side of the footwall sample is attached to the upper pressure bearing plate, the top position of the sliding partition plate on the right side of the footwall sample is attached to the baffle, and the other positions except the top position of the sliding partition plate on the right side of the footwall sample are attached to the plurality of the rollers on the side pressure bearing plate;

arranging the strain gauges along the fault interface on the surface of rock-like samples, arranging acoustic emission detectors on the left and right sides of the surface of rock-like samples, applying speckle on the surface of rock-like samples, aligning the camera with the surface of rock-like samples, connecting the top loading indenter, the bottom loading indenter, the side loading indenter, the strain gauges, the acoustic emission detectors and the camera with computer via signals, respectively;

Step 4. Sample Loading when "in the rock-like sample, placing the footwall sample at the lower left and the hanging wall sample at the upper right", the computer first drives the side loading indenter to apply a lateral stress of the preset pressure to the rock-like sample, and then the computer drives the top loading indenter to apply an axial stress of the preset pressure to the rock-like sample; during the normal dip slip of the hanging wall sample relative to the footwall sample, the side pressure bearing plate moves horizontally to the right, the plurality of the rollers at the lower end of the force transfer column roll along the surface of the upper pressure bearing plate, and the plurality of the rollers at the left end of the side pressure bearing plate roll along the surface of the sliding partition plate on the right side of the hanging wall sample;

when "in the rock-like sample, placing the footwall sample at the lower right and the hanging wall sample at the upper left", the computer first drives the side loading indenter to apply a lateral stress of the preset pressure to the rock-like sample, and then the computer drives the bottom loading indenter to apply an axial stress of the preset pressure to the rock-like sample; during the reverse dip slip of the hanging wall sample relative to the footwall sample, the side pressure bearing plate moves horizontally to the left, the plurality of the rollers at the right end of the bearing seat roll along the surface of the sliding partition plate on the left side of the hanging wall sample; the plurality of the rollers at the lower end of the force transfer column roll along the surface of the upper pressure bearing plate, and the plurality of the rollers at the left end of the side pressure bearing plate roll along the surface of the sliding partition plate on the right side of the footwall sample;

the computer records the real-time axial stress data of the top loading indenter, the real-time support pressure data of the bottom loading indenter, the real-time lateral stress data of the side loading indenter, the real-time strain data monitored by the strain gauge, the real-time acoustic emission data monitored by the acoustic emission detector and the real-time speckle change data monitored by the camera; after loading, removing the rock-like sample, observing and recording the failure of the fault interface on the surface of the rock-like sample.

The advantages of the disclosure are as follows:

The variable dip fault slip simulation test method of the disclosure can prepare rock-like samples with different dip interfaces. The interface types include ordinary fracture interfaces, different roughness interface and low-intensity weak interfaces. It can simulate the slip failure process of faults with different dip angles, as well as the normal dip slip and reverse dip slip of faults. The operation of slip simulation test is convenient, the test data can be collected automatically and accurately to study the slip conditions and mechanical behavior of faults with different dip angles. The sample device applied in the variable dip fault slip simulation test method of the disclosure can not only be used to prepare rock-like samples with different dip interfaces, but also be used as a loading fixture for rock-like samples, which has the dual functions of sample making mold and loading fixture.

DETAILED DESCRIPTION OF PREFERRED EMBODIMENTS

In order to better understand the objectives, features, and advantages of the present invention, the present invention is described below in further detail with reference to the accompanying drawings and specific implementations. It should be noted that without a conflict, the embodiments of this application and the features in the embodiments may be combined with each other.

Many specific details are set forth in the following description to facilitate a full understanding of the present invention. However, the present invention may be implemented in other manners other than those described herein. Therefore, the protection scope of the present invention is not limited by the specific embodiments disclosed below.

In the description of the present invention, it should be understood that if orientation or position relations indicated by the terms such as "inside", "outside", "up", "down", "front", "back" and the like are based on the orientation or position relations shown in the drawings, and the terms are intended only to facilitate the description of the present invention and simplify the description, rather than indicating or implying that the apparatus or element referred to must have a particular orientation and be constructed and operated in the particular orientation, and therefore cannot be construed as a limitation on the present invention.

In the present invention, the terms "first," and "second" are merely for the purpose of description, but cannot be understood as indicating or implying relative importance.

A variable dip fault slip simulation test method of this embodiment is shown in FIGS. 1-8.

A variable dip fault slip simulation test method, The disclosure relates to a variable dip fault slip simulation test method, which adopts a sample device and a loading device.

The sample device includes a bottom plate 11, a sliding partition plate 12, a combined pressure plate 13 and a rotating baffle 14, wherein the sliding partition plate 12 and the combined pressure plate 13 are made of solid steel plate.

The front and rear edges of the bottom plate 11 are provided with sliding grooves 111, the left and right sides of the bottom plate 11 are provided with the sliding partition plates 12, the front and rear ends of the sliding partition plates 12 are provided with sliding blocks 121. The sliding blocks 121 are slidably connected in the sliding grooves 111, and the sliding blocks 121 can slide in the left and right directions along the sliding grooves 111.

The front and rear sides of the bottom plate 11 are provided with the combined pressing plates 13. The combined pressing plates 13 are formed by splicing a plurality of the pressing blocks from head to tail, and the two ends of the combined pressing plate 13 are spliced with the ends of the sliding partition plate 12. Specifically, one pressing block of the adjacent pressing blocks is provided with a T-shaped bump 132, the other pressing block of the adjacent pressing blocks is provided with a T-shaped notch 131, and the adjacent pressure blocks are spliced through the T-shaped bump and the T-shaped notch. Between the pressing block and the end of the sliding partition plate 12, the pressing block is provided with the T-shaped bump, the end of the sliding partition plate 12 is provided with the T-shaped notch, and the pressing block and the end of the sliding partition plate 12 are spliced through the T-shaped bump and the T-shaped notch. In this way, a plurality of pressing blocks can be easily spliced into a combined pressing plate 13 with different lengths, and the combined pressing plate 13 can be easily spliced with the sliding partition plate 12 into whole one. In addition, in the subsequent "loading preparation" step, the combined pressing plate 13 can be easily disconnected at the fault interface.

A rotating baffle 14 is arranged at the middle position of the bottom plate 11, wherein the rotating baffle 14 includes a fixed plate 141 and a sliding plate 142. The fixed plate 141 is rotatably connected with the middle position of the bottom plate 11 and the fixed plate 141 is detachably connected with the bottom plate 11, and the both sides of the fixed plate 141 are slidably connected with a sliding plate 142. The end of the sliding plate 142 is provided with a positioning member 15, wherein the positioning member 15 is detachably connected with the combined pressing plate 13. Specifically, a rotating hole 112 is arranged in the middle of the bottom plate 11, a rotating shaft 143 is provided in the middle of the fixed plate 141, and the rotating shaft is located in the rotating hole 112. one side of the rotating hole 112 is provided with a scale line of 0 to 180°, so that the rotating baffle 14 (the fixed plate 141) is rotated to a preset angle with reference to the scale to simulate a fault inclination with the preset angle. In the present embodiment, the both sides of the fixed plate 141 are provided with hollow cavities, and the sliding plate 142 can stretch out and draw back relative to the hollow cavities.

The positioning member 15 in the present embodiment includes a U-shaped clip 152 and a locking screw 151. The end of the sliding plate 142 is provided with the U-shaped clip, and the locking screw is arranged on one clamping jaw of the U-shaped clip. The U-shaped clip is inverted on the combined pressing plate 13, and the U-shaped clip can slide along the combined pressing plate. When the locking screw is rotated forward, the locking screw and the other clamping jaw of the U-shaped clip clamp the combined pressing plate tightly, and when the locking screw is rotated reversely, the locking screw and the other clamping jaw of the U-shaped clip are separated from the combined pressing plate 13. In this way, the detachable connection of the combined pressing plate 13 and the positioning member 15 can be realized.

The loading device includes a loading support platform, a top loading indenter 22, a top pressure bearing unit, a bottom loading indenter 24, a side loading indenter 25, a side pressure bearing unit, a bearing seat 26, a strain gauge 31, an acoustic emission detector 32, a computer 4 and a camera 5. The loading support platform includes a base 211, a left loading support frame 212, a right loading support frame 213 and an upper loading support frame 214. The left loading support frame 212 is arranged on the left side of the base 211, the right loading support frame 213 is arranged on the right side of the base 211, and the upper loading support frame 214 is provided on the left loading support frame 212 and the right loading support frame 213. The top loading indenter 22 is arranged on the upper loading support frame 214, and the top loading indenter 22 can apply the axial stress of the preset pressure to the rock-like samples (the hanging wall sample 51 and the footwall sample 52) through the top pressure bearing unit. The top bearing unit includes a force transfer column 231, a upper roller 232 and an upper pressure bearing plate 233. The upper end of the force transfer column 231 is connected with the top loading indenter 22, and the lower end of the force transfer column 231 is rotated side by side and is connected with a plurality of the upper rollers 232. And one side of the upper pressure bearing plate 233 is provided with a baffle 234 bent downward. The section shape of the upper pressure bearing plate 233 and the baffle 234 is L-shaped. The top loading indenter 22 applies axial stress downward through the force transfer column 231, the hanging wall sample 51 slides relative to the footwall sample 52, the combined pressing plate 13 on the upper side of the hanging wall sample 51 and the sliding partition plate 12 on the right side of the hanging wall sample 51 or the footwall sample 52 move with the hanging wall sample 51 or the footwall sample 52. The upper pressure bearing plate 233 and the baffle 234 can keep the combined pressing plate 13 and the sliding partition plate 12 in an integrated structure. The upper roller 232 rolls in the horizontal direction along the upper pressure bearing plate 233 to maintain the force transfer column 231 to continuously apply axial stress or limit to the upper pressure bearing plate 233 and the combined pressing plate 13. The bottom loading indenter 24 is set on the base 211. The bottom loading indenter 24 apply axial stress with the preset pressure or limit to the rock-like samples (the hanging wall sample 51 and the footwall sample 52). The bearing seat 26 is arranged on the left loading support frame 212, and the right end of the bearing seat 26 is rotated side by side from top to bottom to connect a plurality of lower rollers 263. The side loading indenter 25 is arranged on the right loading support frame 213. The bearing seat 26, the side loading indenter 25 and the side bearing unit apply the preset pressure on the rock-like samples. And the side pressure bearing unit includes a guide shaft 261, a linear bearing 264, a side pressure bearing plate 262 and the lower rollers 263. The guide shaft 261 is arranged on the right side of the base 211, the linear bearing is arranged on the guide shaft 261, the side pressure bearing plate 262 is arranged on the linear bearing. The left end of the side pressure bearing plate 262 is rotated side by side from top to bottom to connect the plurality of the lower rollers 263. The lower rollers 263 on the bearing seat 26 and the side pressure bearing plate 262 roll along the vertical direction of the bearing seat 26 and the sliding partition plate 12, so as to keep the bearing seat 26 and the pressure bearing plate 262 continuously applying axial stress to the sliding partition plate 12.

A variable dip fault slip simulation test method in the present embodiment includes the following steps:

Step 1. Sample Preparation

The fixed plate 141 (the rotating baffle 14) is rotated to a preset angle to simulate the fault inclination with the preset angle, so as to make the sliding plate 142 draw back relative to the fixed plate 142, connecting the sliding plate 142 with the combined pressing plate 13 for positioning through the positioning member 15. The bottom plate 11, the sliding partition plate 12 and the combined pressing plate 13 form a semi-enclosed cavity, and the rotating baffle 14 separates the semi-enclosed cavity into the first cavity 61 and the second cavity 62. The lubricating oil is applied on the upper surface of the bottom plate 11, the inner wall of the sliding partition plate 12, the inner wall of the combined pressing plate 13, and the surface of the rotating baffle 14, so as to inject the first type of rock material into the first cavity 61 and the second cavity 62. The rotating baffle 14 and the bottom plate 11 are removed after the first type of rock material solidifies into a rock-like sample, and then removing the lubricating oil on the surface of the rock-like sample to maintain the rock-like sample. In this way, the interface 8 type of rock-like sample prepared is ordinary fracture interface.

Wherein, the first type of rock material injected into the the first cavity 61 and the first type of rock material injected into the second cavity 62 are the same material or different materials. When the first type of rock material injected into the first cavity 61 and the first type of rock material injected into the second cavity 62 are the same material, it is used to study the slip of rock stratum with the same lithology on both sides of the fault interface. When the first type of rock material injected into the first cavity 61 and the first type of rock material injected into the second cavity 62 are different materials, it is used to study the slip of rock stratum with the different lithology on both sides of the fault interface.

Figure 1:
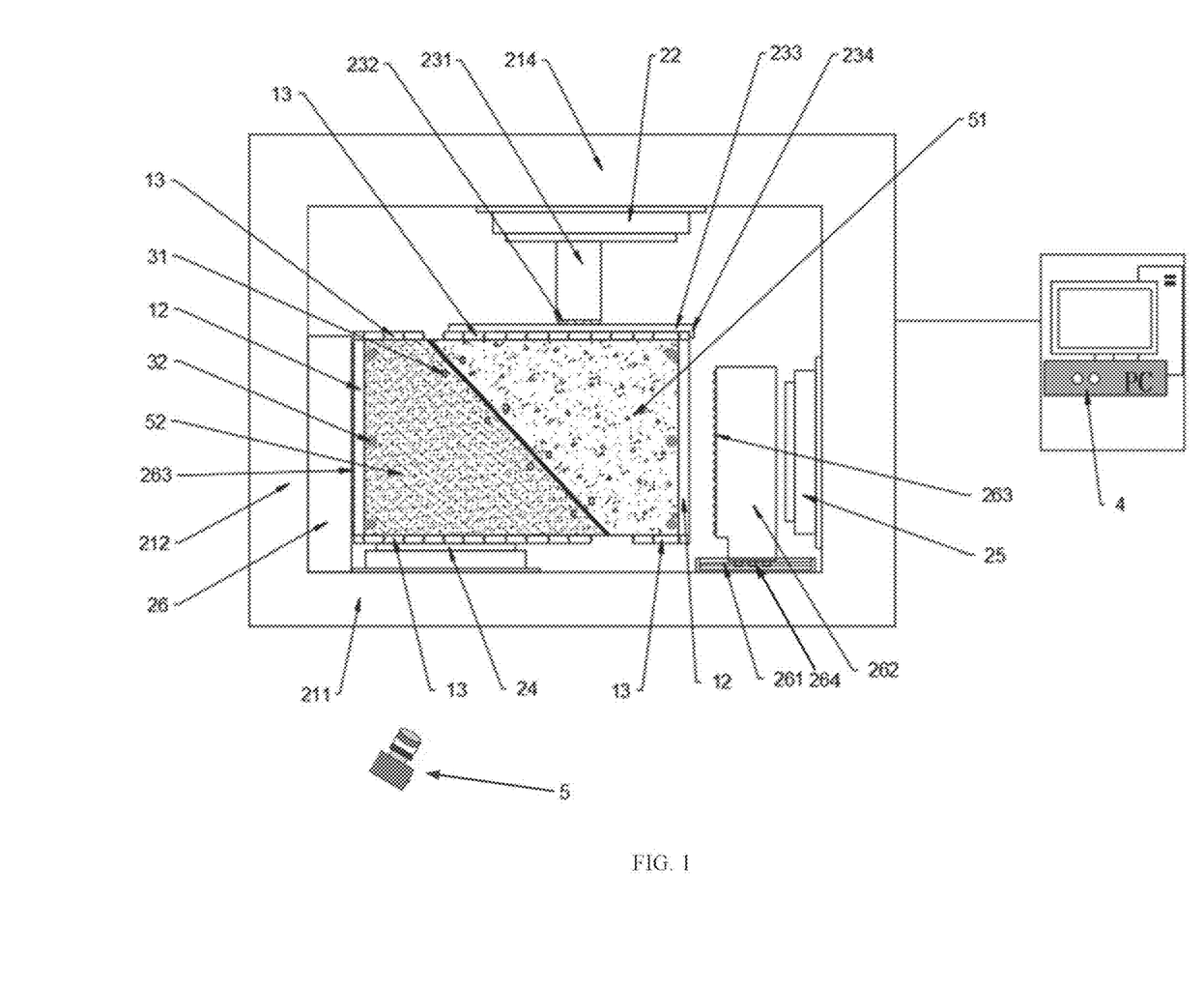
FIG. 1 is a structural diagram I of a rock-like sample, a part of the structure of a sample device and a loading device according to an embodiment of the present disclosure. In the figure, the hanging wall sample tends to positive dip slip relative to the footwall sample.
Figure 2:
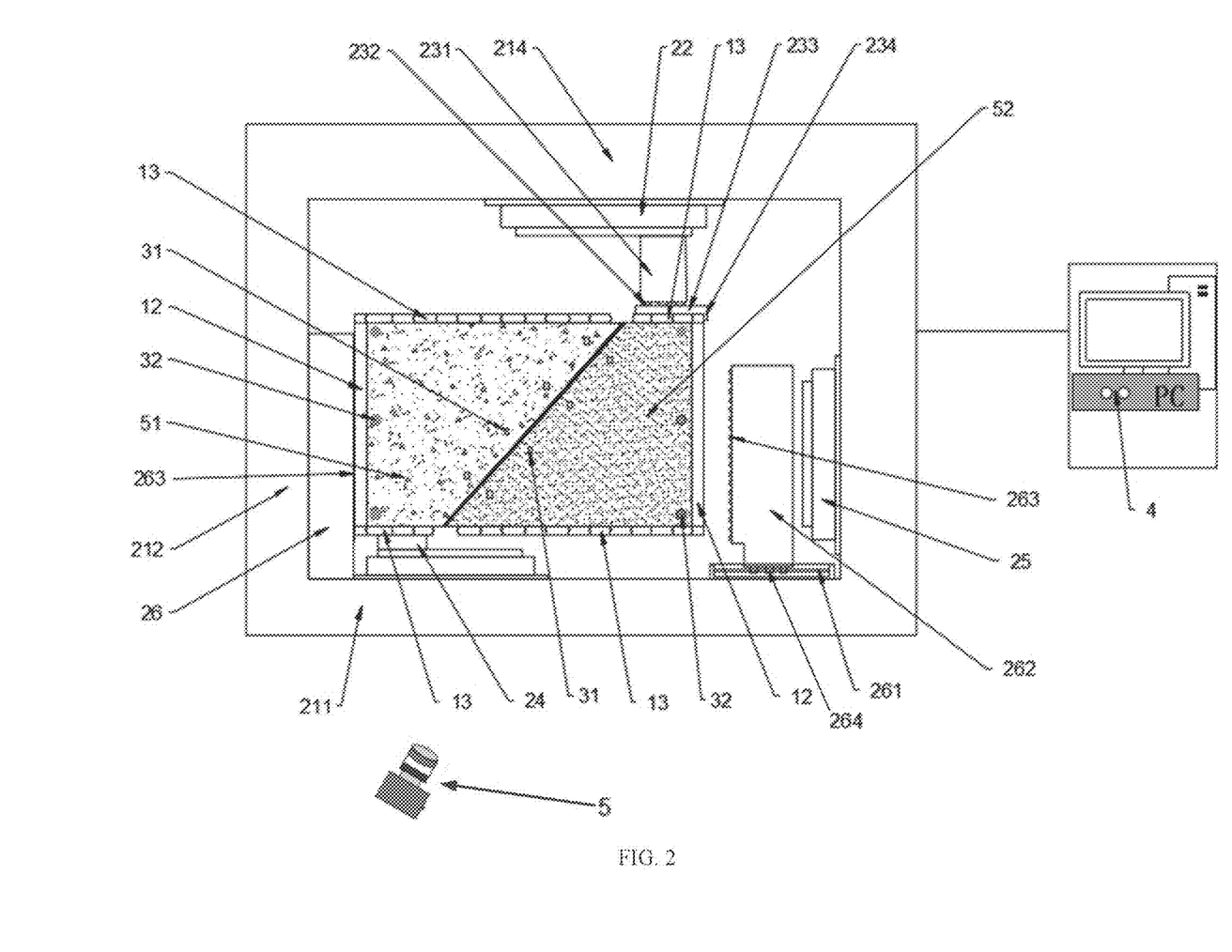
FIG. 2 is the structural diagram II of the rock-like sample, part of the structure of the sample device and the loading device according to the embodiment of the disclosure. In the figure, the hanging wall sample tends to reverse dip slip relative to the footwall sample.
Figure 3:
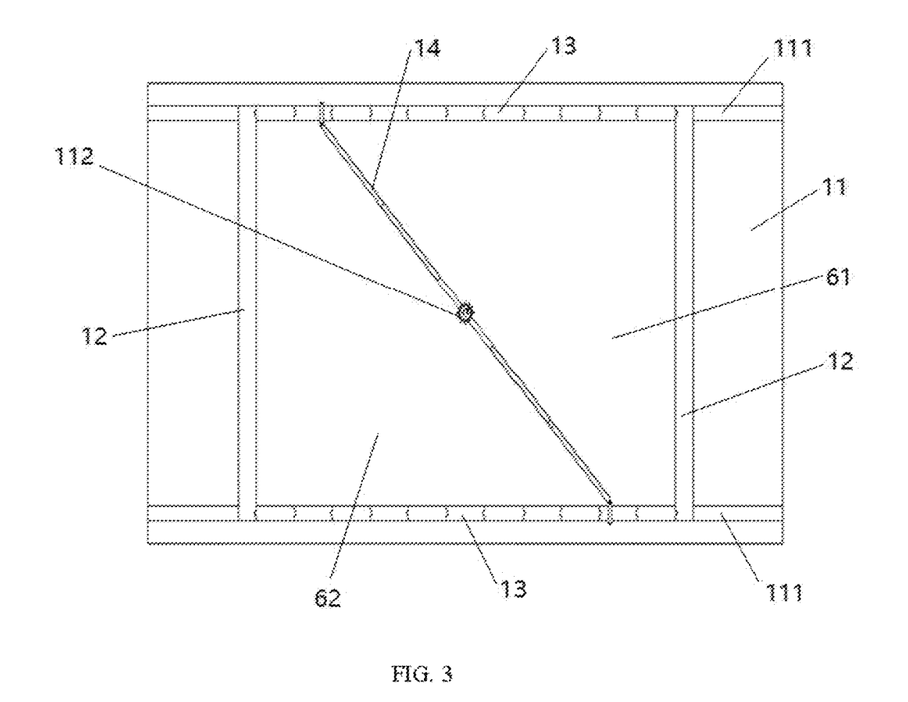
FIG. 3 is a top view of a sample device according to an embodiment of the present disclosure.
Figure 4:
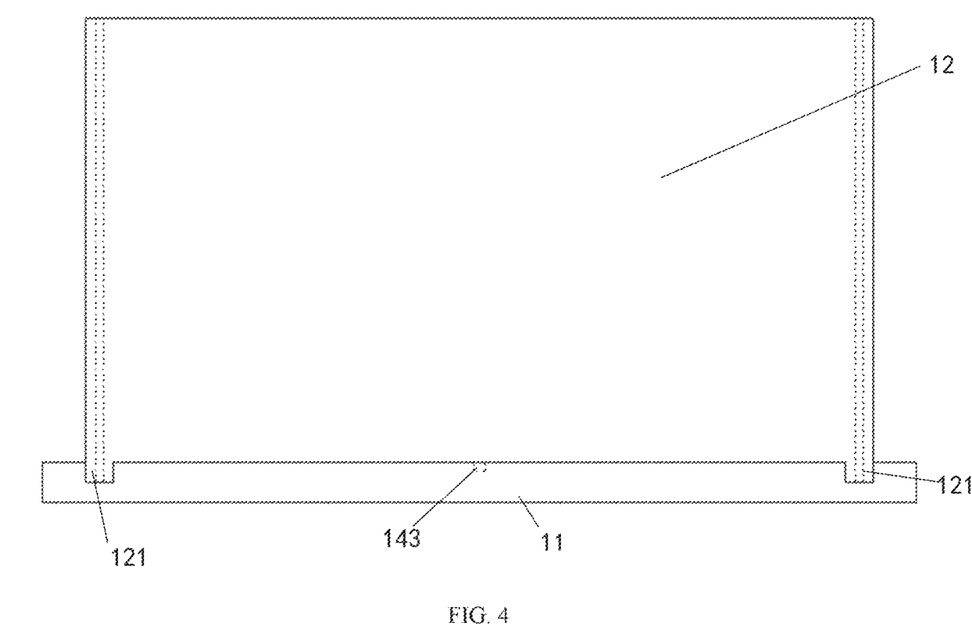
FIG. 4 is a lateral view of the sample device according to the embodiment of the present disclosure.
Figure 5:
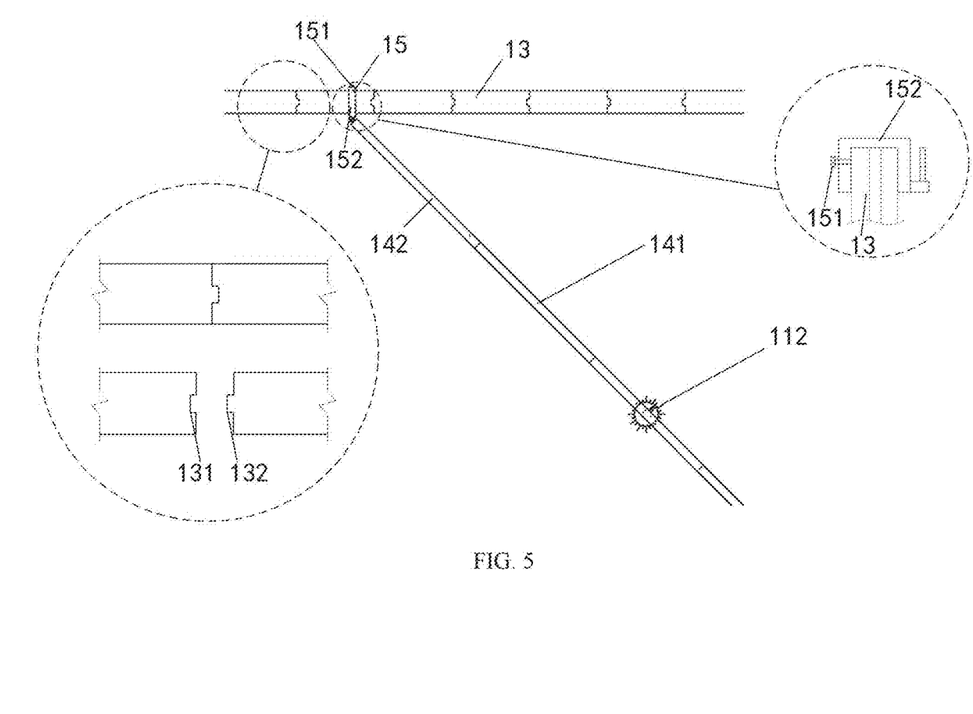
FIG. 5 is a partial structural diagram of the sample device according to the embodiment of the present disclosure.
Figure 6:
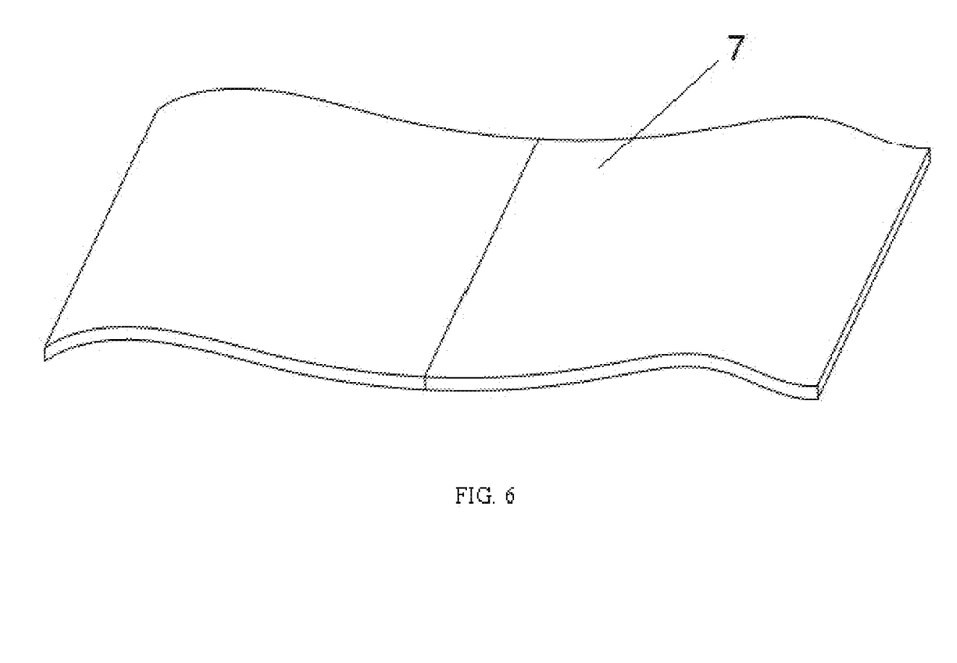
FIG. 6 is a perspective view of a curved thin plate according to the embodiment of the present disclosure.
Figure 7:
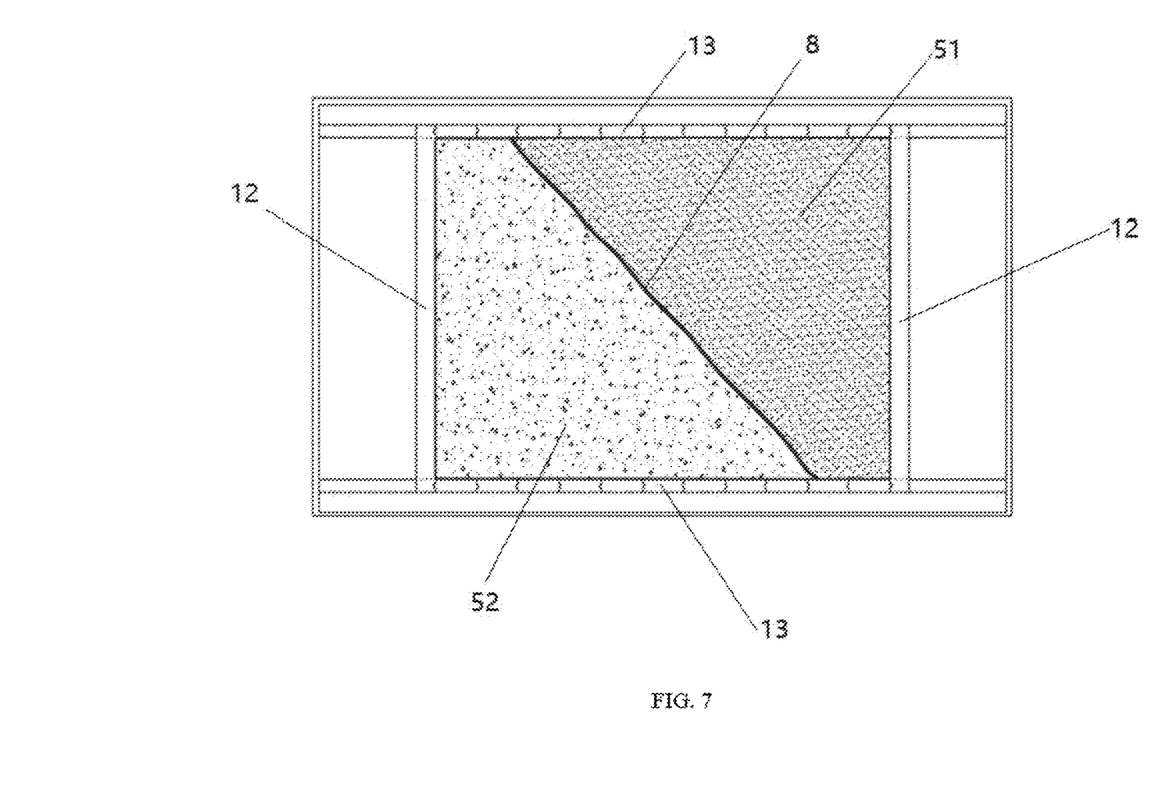
FIG. 7 is a structural diagram of the roughness interface of the fault interface between the the hanging wall sample and the footwall sample in the embodiment of the disclosure, and the roughness interface is set by the curved thin plate.

In step 1, before the first type of rock material solidifies into a rock-like sample, when the first type of rock material is still fluid, after removing the rotating baffle 14, the lubricating oil at the position where the rotating baffle 14 is located originally on the first type of rock material are removed. And a curved thin plate 7 coated with lubricating oil on the surface is put into the position where the rotating baffle 14 is located originally. When the first type of rock material continues to flow or the first type of rock material continues to add, the curved sheet 7 is taken out, to remove the lubricating oil at the position wherein the curved sheet 7 is located originally on the first type of rock material, so as to compact the first type of rock material into a rock-like sample. Wherein, the curved surface shape of the curved sheet 7 corresponds to the curve shape profile of the Barton JRC standard roughness grade. In this way, the type 8 of interface of the prepared rock-like sample are an interface with different roughness, as shown in FIG. 7.

Figure 8:
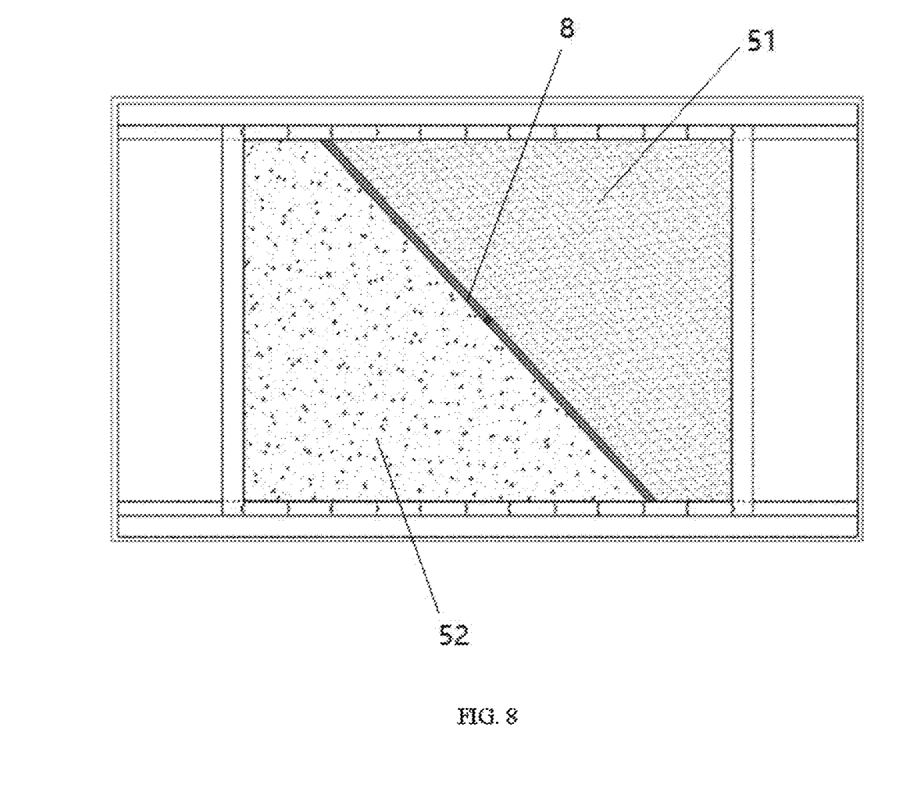
FIG. 8 is a structural diagram of filling a low-intensity weak interface at the fault interface between the hanging wall sample and the footwall sample according to the embodiment of the present disclosure.

In step 1, after the first type of rock material solidifies into a rock-like sample, the lubricating oil on the surface of the rock-like sample is removed after removing the rotating baffle 14 and before removing the bottom plate 11. Filling the position wherein the rotating baffle 14 is located originally in the rock-like sample with the second type of rock material, wherein the strength of the second type of rock material is lower than that of the first type of rock material, and the bottom plate 11 is removed after the second type of rock material is compacted. In this way, the type 8 of interface of the prepared rock-like sample is a low-intensity weak interface, as shown in FIG. 8.

Step 2. Sample Assembly

The rock-like sample in the cavity (the second cavity 62) behind the rotating baffle 14 is defined as the footwall sample 52, and the rock-like sample in the cavity (the first cavity 61) in front of the rotating baffle 14 is defined as the hanging wall sample 51, and the footwall sample 52 and the hanging wall sample 51 together form the rock-like samples. An overlapping interface between the footwall sample 52 and the hanging wall sample 51 is a fault interface. The combined pressing plates 13 are placed on the upper and lower sides of the rock-like samples, and the sliding partition plates 12 are placed on the left and right sides of rock-like samples, the combined pressing plates 13 are spliced with the the sliding partition plates 12, and the combined pressing plates 13 are disconnected at the fault interface.

Step 3. Loading Preparation

In the rock-like samples, the footwall sample 52 is placed at the lower left and the hanging wall sample 51 is placed at the upper right. The combined pressing plate 13 on the lower side of the footwall sample 52 is attached to the bottom loading indenter 24, the sliding partition plate 12 on the left side of the footwall sample 52 is attached to a plurality of the lower rollers 263 on the bearing seat 26. The top pressure bearing unit is placed on the upper side of the hanging wall sample 51, wherein the combined pressing plate 13 on the upper side of the hanging wall sample 51 is attached to the upper pressure bearing plate 233, the top position of the sliding partition plate 12 on the right side of the hanging wall sample 51 is attached to the baffle 234, and the other positions except the top position of the sliding partition plate 12 on the right side of the hanging wall sample 51 are fit with the plurality of the lower rollers 263 on the side pressure bearing plate 263.

Or, in the rock-like samples, the footwall sample 52 is placed at the lower right and the hanging wall sample 51 is placed at the upper left. The combined pressing plate 13 on the lower side of the hanging wall sample 51 is attached to the bottom loading indenter 24, and the sliding partition plate 12 on the left side of the hanging wall sample 51 is attached to the plurality of the lower rollers 263 on the bearing seat 26. The top pressure bearing unit is placed on the upper side of the footwall sample 52. The combined pressing plate 13 on the upper side of the footwall sample 52 is attached to the upper pressure bearing plate 233, the top position of the sliding partition plate 12 on the right side of the footwall sample 52 is attached to the baffle 234, and the other positions except the top position of the sliding partition plate 12 on the right side of the footwall sample 52 are fit with the plurality of the lower rollers 263 on the side pressure bearing plate 262.

The strain gauges 31 are arranged along the fault interface on the surface of rock-like samples, and acoustic emission detectors 32 are arranged on the left and right sides of the surface of rock-like samples. Applying speckles on the surface of rock-like samples, aligning the camera with the surface of rock-like samples, the top loading indenter 22, the bottom loading indenter 24, the side loading indenter 25, the strain gauges 31, the acoustic emission detectors 32 and the camera are connected with computer 4 via signals, respectively.

Step 4. Sample Loading

When "in the rock-like sample, the footwall sample 52 is placed at the lower left and the hanging wall sample 51 is placed at the upper right":

The computer 4 first drives the side loading indenter 25 to apply lateral stress of the preset pressure to the rock-like sample, and then the computer 4 drives the top loading indenter 22 to apply axial stress of the preset pressure to the rock-like sample. At this time, the bottom loading indenter 24 acts as a displacement constraint. During the normal dip slip of the hanging wall sample 51 relative to the footwall sample 52, the side pressure bearing plate 262 is moved horizontally to the right, the plurality of the upper rollers 232 at the lower end of the force transfer column 231 roll along the surface of the upper pressure bearing plate 233, and the plurality of the lower rollers 263 at the left end of the side pressure bearing plate 262 roll along the surface of the sliding partition plate 12 on the right side of the hanging wall sample 51. In this way, the hanging wall sample 51 is simulated to simulate the normal dip slip of the fault.

When "in the rock-like sample, the footwall sample 52 is placed at the lower right and the hanging wall sample 51 is placed at the upper left":

The computer 4 first drives the side loading indenter 25 to apply lateral stress of the preset pressure to the rock-like sample, and then the computer 4 drives the bottom loading indenter 24 to apply axial stress of the preset pressure to the rock-like sample. At this time, the top loading indenter 22 acts as a displacement constraint. During the reverse dip slip of the hanging wall sample 51 relative to the footwall sample 52, the side pressure bearing plate 262 is moved horizontally to the left, the plurality of the lower rollers 263 at the right end of the bearing seat 26 roll along the surface of the sliding partition plate 12 on the left side of the hanging wall sample 51. The plurality of the upper rollers 232 at the lower end of the force transfer column 231 roll along the surface of the upper pressure bearing plate 233, and the plurality of the lower rollers 263 at the left end of the side pressure bearing plate 262 roll along the surface of the sliding partition plate 12 on the right side of the footwall sample 52. In this way, the hanging wall sample 51 is simulated to simulate the reverse dip slip of the fault.

The computer 4 records the real-time axial stress data of the top loading indenter 22, the real-time support pressure data of the bottom loading indenter 24, the real-time lateral stress data of the side loading indenter 25, the real-time strain data monitored by the strain gauge 31, the real-time acoustic emission data monitored by the acoustic emission detector 32 and the real-time speckle change data monitored by the camera. After loading, removing the rock-like samples, observing and recording the failure of the fault interface on the surface of the rock-like samples. So far, the present embodiment has been described in detail in combination with the accompanying drawings. According to the above description, those skilled in the art should have a clear understanding of the variable dip fault slip simulation test method of the present disclosure. The variable dip fault slip simulation test method of the disclosure can prepare rock-like samples with different dip interfaces. The interface types include ordinary fracture interfaces, different roughness interface and low-intensity weak interfaces. It can simulate the slip failure process of faults with different dip angles, as well as the normal dip slip and reverse dip slip of faults. The operation of slip simulation test is convenient, the test data can be collected automatically and accurately to study the slip conditions and mechanical behavior of faults with different dip angles. Besides, in the variable dip fault slip simulation test method of the present disclosure, the applied sample device can be used not only to prepare rock-like samples with different dip interfaces, but also can be used as a loading fixture for rock-like samples, which has the dual functions of sample making mold and loading fixture.

The above are merely preferred embodiments of the present invention and are not intended to limit the present invention. The present invention may be subject to changes and variations for those skilled in the art. Any modifications, equivalent replacements, and improvements made within the spirit and principles of the present invention shall all be encompassed in the protection scope of the present invention.

What is claimed is:

1. A variable dip fault slip simulation test method, which adopts a sample device and a loading device;

the sample device comprises a bottom plate, a sliding partition plate, a combined pressing plate and a rotating baffle; front and rear edges of the bottom plate are provided with sliding grooves, left and right sides of the bottom plate are provided with the sliding partition plates, front and rear ends of the the sliding partition plates are provided with sliding blocks, and the sliding blocks are slidably connected in the sliding grooves; the front and rear sides of the bottom plate are provided with the combined pressing plates, wherein the combined pressing plates are formed by splicing a plurality of the pressing blocks from head to tail, and two ends of the combined pressing plate are spliced with ends of the sliding partition plate; a rotating baffle is arranged at a middle position of the bottom plate, wherein the rotating baffle comprises a fixed plate and a sliding plate, the fixed plate is rotatably connected with the middle position of the bottom plate and the fixed plate is detachably connected with the bottom plate, and both sides of the fixed plate are slidably connected with a sliding plate; an end of the sliding plate is provided with a positioning member, wherein the positioning member is detachably connected with the combined pressing plate;

the loading device comprises a loading support platform, a top loading indenter, a top pressure bearing unit, a bottom loading indenter, a side loading indenter, a side pressure bearing unit, a bearing seat, a strain gauge, an acoustic emission detector, a computer and a camera; the loading support platform comprises a base, a left loading support frame, a right loading support frame and an upper loading support frame; the left and right sides of the base are respectively provided with the left loading support frame and the right loading support frame, and the upper loading support frame is provided on the left loading support frame and the right loading support frame; a top loading indenter is arranged on the upper loading support frame; the top bearing unit comprises a force transfer column, a roller and an upper pressure bearing plate, an upper end of the force transfer column is connected with the top loading indenter, a lower end of the force transfer column is rotated side by side and is connected with a plurality of rollers, and one side of the upper pressure bearing plate is provided with a baffle bent downward; the bottom loading indenter is set on the base; the bearing seat is arranged on the left loading support frame, and a right end of the bearing seat is rotated side by side from top to bottom to connect a plurality of rollers; a side loading indenter is arranged on the right loading support frame; the side pressure bearing unit comprises a guide shaft, a linear bearing, a side pressure bearing plate and the rollers, the guide shaft is arranged on a right side of the base, the linear bearing is arranged on the guide shaft, the side pressure bearing plate is arranged on the linear bearing, and a left end of the side pressure bearing plate is rotated side by side from top to bottom to connect a plurality of rollers;

the method comprises the following steps:

step 1. sample preparation rotating the fixed plate to a preset angle to simulate the fault inclination with the preset angle, so as to make the sliding plate stretch out and draw back relative to the fixed plate; connecting the sliding plate with the combined pressing plate for positioning through the positioning member; wherein the bottom plate, the sliding partition plate and the combined pressing plate form a semi-enclosed cavity, and the rotating baffle separates the semi-enclosed cavity into two cavities; applying lubricating oil on an upper surface of the bottom plate, an inner wall of the sliding partition plate, an inner wall of the combined pressing plate, and a surface of the rotating baffle, injecting a first type of rock material into the two cavities, removing the rotating baffle and the bottom plate after the first type of rock material solidifies into a rock-like sample, removing the lubricating oil on the surface of the rock-like sample, and maintaining the rock-like sample;

wherein, the first type of rock material injected into the two cavities is the same material or different materials;

step 2. sample assembly defining the rock-like sample in the cavity behind the rotating baffle as a footwall sample, and defining the rock-like sample in the cavity in front of the rotating baffle as the hanging wall sample, and the footwall sample and the hanging wall sample together form the rock-like sample; an overlapping interface between the footwall sample and the hanging wall sample is a fault interface, placing the combined pressing plates on upper and lower sides of the rock-like samples, placing the sliding partition plates on left and right sides of rock-like samples, splicing the combined pressing plate with the the sliding partition plate, wherein the combined pressing plate is disconnected at the fault interface;

step 3. loading preparation in the rock-like samples, placing the footwall sample at the lower left and the hanging wall sample at the upper right, wherein the combined pressing plate on the lower side of the footwall sample is attached to the bottom loading indenter, the sliding partition plate on the left side of the footwall sample is attached to a plurality of the rollers on the bearing seat; placing the top pressure bearing unit on the upper side of the hanging wall sample, wherein the combined pressing plate on the upper side of the hanging wall sample is attached to the upper pressure bearing plate, the top position of the sliding partition plate on the right side of the hanging wall sample is attached to the baffle, and the other positions except the top position of the sliding partition plate on the right side of the hanging wall sample are attached to the plurality of rollers on the side pressure bearing plate;

or, in the rock-like samples, placing the footwall sample at the lower right and the hanging wall sample at the upper left; wherein the combined pressing plate on the lower side of the hanging wall sample is attached to the bottom loading indenter, and the sliding partition plate on the left side of the hanging wall sample is attached to the plurality of the rollers on the bearing seat; placing the top pressure bearing unit on the upper side of the footwall sample, wherein the combined pressing plate on the upper side of the footwall sample is attached to the upper pressure bearing plate, the top position of the sliding partition plate on the right side of the footwall sample is attached to the baffle, and the other positions except the top position of the sliding partition plate on the right side of the footwall sample are attached to the plurality of the rollers on the side pressure bearing plate;

arranging the strain gauges along the fault interface on the surface of rock-like samples, arranging acoustic emission detectors on the left and right sides of the surface of rock-like samples, applying speckle on the surface of rock-like samples, aligning the camera with the surface of rock-like samples, connecting the top loading indenter, the bottom loading indenter, the side loading indenter, the strain gauges, the acoustic emission detectors and the camera with computer via signals, respectively;

step 4. sample loading when the footwall sample is placed at the lower left and the hanging wall sample is placed at the upper right, the computer first drives the side loading indenter to apply a lateral stress of the preset pressure to the rock-like sample, and then the computer drives the top loading indenter to apply an axial stress of the preset pressure to the rock-like sample; during the normal dip slip of the hanging wall sample relative to the footwall sample, the side pressure bearing plate moves horizontally to the right, the plurality of the rollers at the lower end of the force transfer column roll along the surface of the upper pressure bearing plate, and the plurality of the rollers at the left end of the side pressure bearing plate roll along the surface of the sliding partition plate on the right side of the hanging wall sample;

when the footwall sample is placed at the lower right and the hanging wall sample is placed at the upper left, the computer first drives the side loading indenter to apply a lateral stress of the preset pressure to the rock-like sample, and then the computer drives the bottom loading indenter to apply an axial stress of the preset pressure to the rock-like sample; during the reverse dip slip of the hanging wall sample relative to the footwall sample, the side pressure bearing plate moves horizontally to the left, the plurality of the rollers at the right end of the bearing seat roll along the surface of the sliding partition plate on the left side of the hanging wall sample; the plurality of the rollers at the lower end of the force transfer column roll along the surface of the upper pressure bearing plate, and the plurality of the rollers at the left end of the side pressure bearing plate roll along the surface of the sliding partition plate on the right side of the footwall sample;

the computer records the real-time axial stress data of the top loading indenter, the real-time support pressure data of the bottom loading indenter, the real-time lateral stress data of the side loading indenter, the real-time strain data monitored by the strain gauge, the real-time acoustic emission data monitored by the acoustic emission detector and the real-time speckle change data monitored by the camera; after loading, removing the rock-like sample, observing and recording the failure of the fault interface on the surface of the rock-like sample.

2. The variable dip fault slip simulation test method according to claim 1, wherein the positioning member comprises a U-shaped clip and a locking screw, the end of the sliding plate is provided with the U-shaped clip, and the locking screw is arranged on one clamping jaw of the U-shaped clip; the U-shaped clip is inverted on the combined pressing plate, and the U-shaped clip is able to slide along the combined pressing plate; the locking screw is rotated forward, so that the locking screw and the other clamping jaw of the U-shaped clip clamp the combined pressing plate; and the locking screw is rotated reversely, the locking screw and the other clamping jaw of the U-shaped clip are separated from the combined pressing plate.

3. The variable dip fault slip simulation test method according to claim 1, wherein a rotating hole is arranged in a middle of the bottom plate, a rotating shaft is provided in a middle of the fixed plate, and the rotating shaft is located in the rotating hole.

4. The variable dip fault slip simulation test method according to claim 3, wherein one side of the rotating hole is provided with a scale line of 0 to 180°.

5. The variable dip fault slip simulation test method according to claim 1, wherein one pressing block of the adjacent pressing blocks is provided with a T-shaped bump, the other pressing block of the adjacent pressing blocks is provided with a T-shaped notch, and the adjacent pressure blocks are spliced through the T-shaped bump and the T-shaped notch; between the pressing block and the end of the sliding partition plate, the pressing block is provided with the T-shaped bump, the end of the sliding partition plate is provided with the T-shaped notch, and the end of the pressing block and the sliding partition plate are spliced through the T-shaped bump and the T-shaped notch.

6. The variable dip fault slip simulation test method according to claim 1, wherein both sides of the fixed plate are provided with hollow cavities, and the sliding plate is able to stretch out and draw back relative to the hollow cavities.

7. The variable dip fault slip simulation test method according to claim 1, wherein the sliding partition plate and the combined pressing plate are made of solid steel plate.

* * * * *